United States Patent
Cipywnyk

[11] 3,979,946
[45] Sept. 14, 1976

[54] ULTRASONIC PLATE INSPECTION SYSTEM

[75] Inventor: Harold Z. Cipywnyk, Burlington, Canada

[73] Assignee: The Steel Company of Canada, Limited, Hamilton, Canada

[22] Filed: May 27, 1975

[21] Appl. No.: 580,610

[30] Foreign Application Priority Data
June 10, 1974 Canada.................................. 202015

[52] U.S. Cl............................................ 73/71.5 US
[51] Int. Cl.².......................................... G01N 29/04
[58] Field of Search............ 73/71.5 US, 67.5–67.8; 310/8.3

[56] References Cited
UNITED STATES PATENTS

| | | | |
|---|---|---|---|
| 3,190,112 | 6/1965 | Beaujard et al................. | 73/71.5 US |
| 3,303,691 | 2/1967 | Beaujard et al................. | 73/71.5 US |
| 3,646,806 | 3/1972 | Yamaguchi..................... | 73/71.5 US |

*Primary Examiner*—James J. Gill
*Attorney, Agent, or Firm*—Sim & McBurney

[57] ABSTRACT

This invention provides for the ultrasonic testing of hot, moving metal plate, to detect faults therein. A testing shoe has a surface intended to be juxtaposed against the metal plate, and includes an ultrasonic probe member with an adjacent face parallel with but slightly recessed from the shoe surface. An internal cooling chamber encircles the probe member and has an outlet adjacent the generating face. Cooling liquid is conveyed to the cooling chamber, and exits across the generating face and along a pre-cooling channel in the shoe surface extending away from the probe member in the direction opposite the direction of movement of the metal plate with respect to the shoe.

16 Claims, 6 Drawing Figures

ULTRASONIC PLATE INSPECTION SYSTEM

This invention relates generally to ultrasonic systems for detecting internal defects or flaws in material such as metal plate, and has to do particularly with a shoe adapted to be placed in sliding, juxtaposed relationship with moving plate material for the ultrasonic detection of flaws therein.

BACKGROUND OF THIS INVENTION

In the manufacture of steel plate, a poured and solidified ingot first undergoes an initial rolling operation in a rolling mill which brings it down to a thickness in the order of two inches to four inches. The slab thus formed can subsequently be rolled into steel plate with a thickness in the region of one-quarter inch to one and one-quarter inch. Almost invariably, the slab is hot-rolled, which requires that it be re-heated up to a temperature of about 1,200°C in a suitable furnace, and then passed through the plate mill.

Depending upon the length of time elapsing between the removal of the slab from the re-heating furnace and the point at which ultrasonic testing is to be carried out, the surface temperature of the plate area to be tested may be anywhere from ambient to about 700°C.

The basic process by which steel plate is tested for internal flaws such as laminations resulting from the rolling process involves the generation of an ultrasonic signal (longitudinal wave-propagation), together with some means for transmitting the ultrasonic signal into the steel plate without high losses. The surfacee of the steel plate act as reflection surfaces for the propagated waves, particularly the surface remote from the generation point, and by timing the lapse between the generation of the signal and the detection of the echo it is possible to distinguish between a plate area which is sound and without flaws, and one which, for example, contains a lamination or other discontinuity at a central point between its two surfaces. Any such lamination would act as a reflection surface, and the time-lapse between generation and echo detection would decrease. It is possible to display the two signals on an oscilloscope utilizing the standard synchronization techniques, so that visual identification of laminations and other flaws can be carried out.

In order to be able to transmit the ultrasonic signal directly into the material of the steel plate, a good coupling must take place, and this is ordinarily accomplished by establishing a column or layer of water between the ultrasonic signal generating surface and the nearer surface of the metal plate. Where excessive plate temperatures are encountered, the water between the ultrasonic generating surface and the plate surface can contribute to cooling to some extent, but it is important to understand that with inadequate or unstable water flow, a hot plate surface may cause boiling or bubbling, or may in some other way disrupt the coupling qualities of the liquid.

SUMMARY OF THE PRIOR ART

In one prior art method, an ultrasonic probe is coupled to the continuously moving hot steel plate by means of laminar flow water columns. In this prior art method, the probe is spaced several inches from the plate, and the water flows perpendicularly toward the plate in the direction of propagation of the ultrasonic signal. Generally, the maximum plate temperature that can be accommodated with this method is about 220°C, and where pre-cooling is used, plates with surface temperatures up to 300°C may be tested. About 21 gpm of water is required for each test channel with this method.

In another prior art method, ultrasonic coupling is maintained by a flow of water through a 1 mm gap between a probe and the plate surface. The maximum temperature that can be accommodated by this process is about 200°C without pre-cooling, and about 350°C with pre-cooling. Roughly 14 litres/min of water is required for each test channel in this method.

Essentially, the basic drawback of the two prior art methods discussed briefly above relates to the fact that the pre-cooling water must be uniformly applied over the width of the plate both on the top and bottom surfaces in order to be effective. The water which is applied to the top surface of the plate in the temperature range of 100°C to about 220°C (the region between nucleate boiling and film boiling) tends to collect and remain in a depression in the plate caused by the thermal distortion of the plate surface. The plate continues to distort and remains in the distorted condition until all of the water has evaporated. This condition can be detrimental to the final shape of the plate and is a hazard to personnel working in the area. Large quantities of steam are generated by this method. Means are often provided for wiping the water off the plate, and these means can include rolls, air knives, etc. Such apparatus is usually massive and noisy. When temperatures above 220°C are encountered, film boiling takes place and causes the excess water to run off the plate very rapidly, presenting a hazard to personnel and equipment. This necessitates massive steam and water collection equipment.

Although the prior art does include some attempt to overcome the foregoing problems relating to pre-cooling water, these too have certain drawbacks and shortcomings. One such prior art development involves the provision of an ultrasonic testing shoe with a contact surface adapted to be pressed in surface-to-surface contact with the upper face of the moving hot metal plate. The shoe includes a large, central cylindrical bore hole through which the ultrasonic probe is inserted. The bore hole is larger than the probe, and defines therewith an annular probe-cooling chamber to which is supplied cooling water through a suitable inlet. No specific outlet is provided from the cooling chamber, and water must exit from this chamber between the mating surfaces of the plate and the shoe. To a large extent, this cooling water would exit in the downstream direction with respect to the plate movement, under the urging of the plate. This prior art device also includes a separate pre-cooling chamber which is fed from a separate inlet and which communicates with a channel in the contact surface of the shoe, which channel extends in the upstream direction radially away from the probe. This provision is made to permit pre-cooling water to be passed into the pre-cooling chamber and thence out along the channel in contact with the moving metal plate just upstream of the probe.

While the last-described prior art development does represent an improvement over previous methods of ultrasonically testing hot metal plates, it nonetheless has the serious drawback that there is no opening or outlet expressly provided for water leaving the cooling chamber which annularly surrounds the ultrasonic probe. Because of this, the rate of cooling water throughout is rather limited, and can only be increased by an increased flow-out between the mating surfaces of the metal plate and the shoe, which in turn would raise the shoe away from the metal plate, which in turn would reduce the "tightness" of the conduit defined between the pre-cooling channel and the surface of the plate (that fed from a separate, secondary inlet).

Additionally, the prior art development just described shares a failing which is common to all prior art testing shoes of which applicant is aware, namely the tendency for the contacting surface of the testing shoe to wear unevenly with the greater wear taking place at the edge first contacted by a given portion of the moving metal plate. This causes a "pitching" action of the shoe whereby it becomes angulated with respect to the plane of the hot metal plate, and this in turn raises problems with the ultrasonic signal detection portion of the apparatus, which requires that the generating face of the probe member and the plane of the hot metal plate be essentially parallel.

OBJECTS OF THIS INVENTION

Accordingly, it is an object of this invention to provide an ultrasonic testing shoe in which all of the foregoing prior art disadvantages are minimized or eliminated.

BRIEF DESCRIPTION OF THE INVENTION

Accordingly, this invention provides a shoe for ultrasonically testing hot, moving metal plate for faults, the shoe comprising: a body member having a surface adapted to be juxtaposed with respect to the metal plate, an ultrasonic probe member fixed in the body member and having a generating face parallel with and slightly recessed from said body surface, the body member defining an internal cooling chamber encircling said probe member and having an outlet adjacent the generating face of the probe member, an inlet passageway in said body member for conveying cooling liquid to said cooling chamber, and a pre-cooling channel in said surface extending away from the probe member remote from said outlet opening, whereby cooling liquid admitted to said cooling chamber through said inlet passageway can cool said probe member and then pass out of said outlet, across said generating face to permit transmission of the ultrasonic signal to the metal plate, and along the channel to cool the metal plate.

A further feature disclosed herein relates to the provision, on an ultrasonic testing shoe of the kind described above, of wheel means mounted on the body member, the wheel means having peripheries for contacting and rolling on the metal plate but being initially affixed to the body member such that the contacting portions of the peripheries are slightly recessed with respect to the surface of the body member, whereby when the shoe is urged against the moving metal plate said surface is gradually worn down until the peripheries of the wheel means contact the metal plate and restrain further wearing down of the surface.

Additionally there is disclosed herein a method of ultrasonically testing a hot, moving metal plate for faults, the method including the steps of resiliently urging against one surface of the moving metal plate a flat surface of a body member in which is mounted an ultrasonic probe member having a generating face slightly recessed from the flat surface and thus spaced from said moving metal plate, passing cooling liquid continuously into a cooling chamber within said body member and encircling said probe member, thereby cooling said probe member, passing cooling liquid out of said chamber through an outlet in said flat surface adjacent and downstream of said probe member with respect to the direction of movement of the metal plate, passing cooling liquid from said outlet across said generating face to permit transmission of ultrasonic signals to the moving metal plate, and passing the cooling liquid from said generating face along a channel recessed in said flat surface and extending upstream with respect to the direction of movement of the metal plate, thereby to pre-cool the hot metal plate before it comes adjacent said generating face.

There is further disclosed a method of ensuring a close tolerance between the moving metal plate and a substantially stationary shoe intended for testing the moving metal plate and having a surface adapted to be juxtaposed with respect to the metal plate, the method comprising the steps: mounting freely-rotating rolling members on the shoe such that the peripheries of the rolling members are slightly recessed with respect to said surface of the shoe, and urging the shoe resiliently against the moving metal plate to gradually wear down said surface until the peripheries of the rolling members contact and roll against the metal plate, and thus restrain further wearing down of said surface.

BRIEF DESCRIPTION OF THE DRAWINGS

One embodiment of this invention illustrated in the accompanying drawings, in which like numerals denote like parts throughout the several views, and in which.

PARTICULAR DESCRIPTION OF THE DRAWINGS

Figure 1:
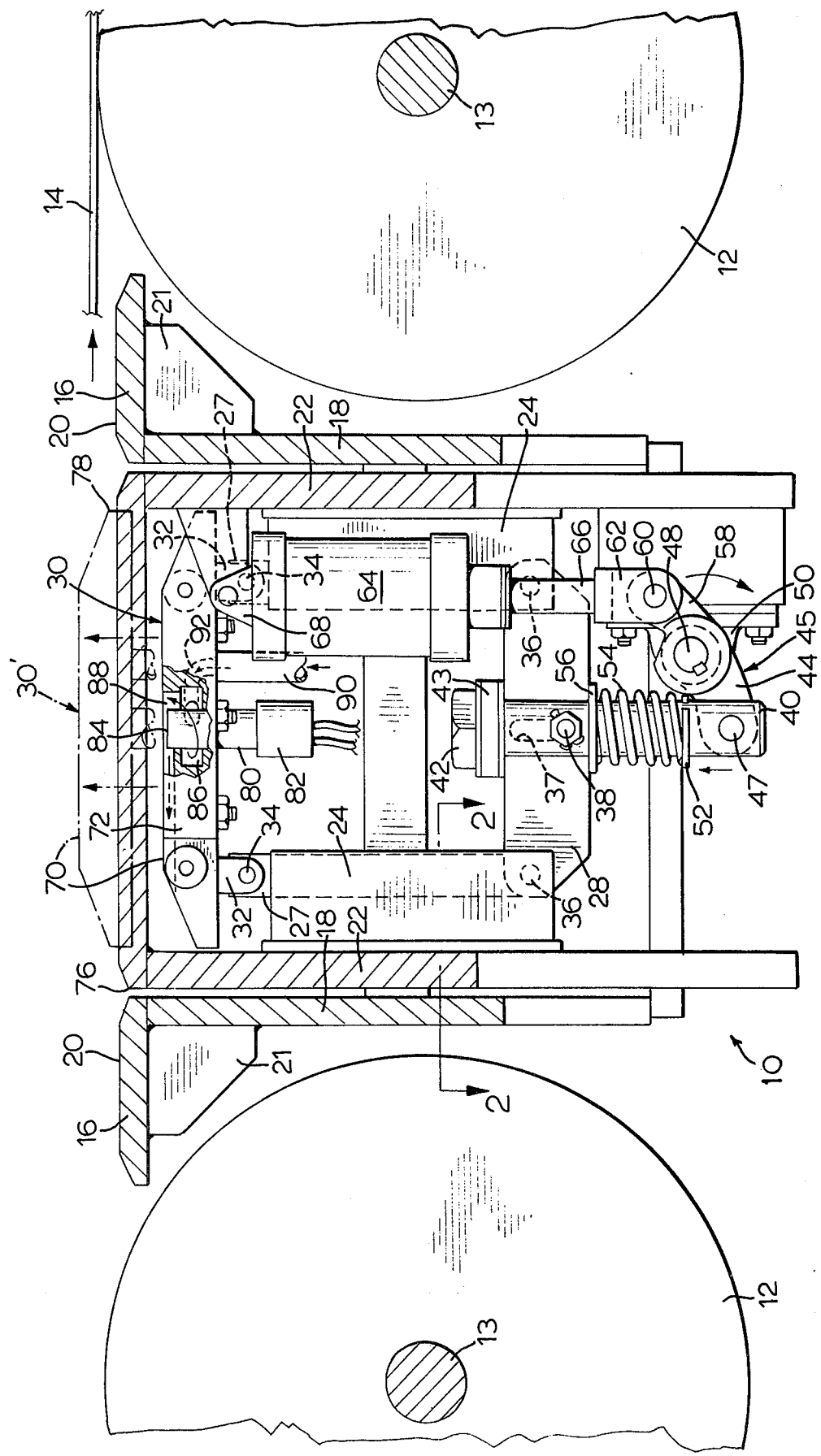
FIG. 1 is a vertical sectional view of apparatus for ultrasonically testing hot metal plate for faults.

Referring first to FIG. 1, the ultrasonic testing apparatus shown generally at 10 is positioned between two transporter rolls 12 mounted on central shafts 13 and supporting for horizontal translation from left to right a section of hot metal plate 14 which is assumed to have just emerged from a plate-rolling mill.

The apparatus 10 includes side flange members 16 supported at the upper end of upstanding plate members 18, and exhibiting upper slide surfaces 20 which are slightly recessed (downwardly) with respect to a hypothetical plane tangent simultaneously to both transporter rolls 12. Bracket members 21 serve to support the side flange members 16 rigidly with respect to the plate members 18. The plate members 18 are in turn supported (by means not shown in detail) in such a way as to remain rigid with respect to and between the rotational axes of the two transporter rolls 12.

Inwardly adjacent the upstanding plate members 18 are two vertical frame members 22, which are thus also fixed with respect to and between the rotational axes of the transporter rolls 12.

Figure 2:
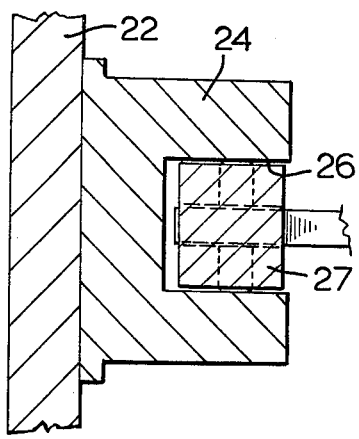
FIG. 2 is a horizontal sectional view of a portion of the apparatus of FIG. 1, taken at the line 2—2.

Firmly supported from the inner surfaces of the vertical frame members 22 are two upstanding C-track members 24, of which the left-hand one is shown in horizontal section in FIG. 2. Vertically slidable within the central recess 26 of each C-track member 24 is a slide bar 27, the two slide bars 27 being connected together at their lower ends by a lower rocker link 28, and being connected together at the upper ends through an ultrasonic testing shoe 30 which will be described in greater detail below. The ultrasonic testing shoe 30 has two downwardly projecting bracket members 32 which are rigidly connected to the ultrasonic testing shoe 30, and which are freely pivoted through pins 34 to the slide bars 27. The lower rocker link 28 is also connected for free pivotal motion to the lower ends of the slide bars 27 through pins 36.

It will thus be seen that the two slide bars 27, the lower rocker link 28 and the ultrasonic testing shoe 30 (including the bracket members 32) constitute a four-sided parallelogram linkage. Although this parallelogram linkage is shown in rectangular configuration in FIG. 1, it will be understood that, because the slide bars 27 are independently slidable within their respective C-track members 24, it is possible for either end of the ultrasonic testing shoe 30 to rise to some extent with respect to the other end, which tilting would also be undergone by the lower rocker link 28.

The lower rocker link 28 has a vertical slot 37 through which passes a pin 38 fixed diametrally in a vertical shank member 40. As illutrated in FIG. 1, the vertical shank member 40 is in the form of a cylindrical shaft with two diametral slots provided one in each end. The vertical slot in the upper end slidingly receives the lower rocker link 28, and the upper portion of the vertical shank member 40 is externally threaded to receive a nut 42. Between the nut 42 and the lower rocker link 28 is a washer assembly 43, which may advantageously include a resilient intermediate washer sandwiched between two rigid washers.

The slot in the lower end of the vertical shank member 40 is adapted to receive one end 44 of a lever arm 45, the end 44 being pivoted for free rotation to the vertical shank member 40 through a pin 47. The lever arm 45 is pivoted through a pin 48 about a bracket 50 which is fixed with respect to the frame.

At an intermediate location along its length, the vertical shank member 40 has a peripheral groove in which a split washer 52 is lodged. A coil spring 54 has its lower end resting against the split washer 52 and supports at its upper end a washer 56 which is slidable with respect to the vertical shank member 40. The washer 56 is urged against the under edge of the lower rocker link 28 by the upper end of the coil spring 54.

In the position shown in solid lines in FIG. 1, the pin 38 lies at the lower end of the vertical slot 37 (dotted in FIG. 1) which is centrally located in the lower rocker link 28. The coil spring 54 is under compression at all times, and is urging the lower rocker link 28 to its uppermost position with respect to the vertical shank member 40 in FIG. 1. It will be noted that the ultrasonic testing shoe 30 in FIG. 1, as shown in solid lines, is withdrawn or recessed with respect to the hot metal plate 14 (i.e., with respect to the horizontal plane which is simultaneously tangent to both transporter rolls 12.) For this reason, there is no downward pressure against the ultrasonic testing shoe, or against the lower rocker link 28, and this permits the coil spring 54 to urge the lower rocker link 28 to its uppermost position as illustrated in FIG. 1.

Attention is again directed to the lever arm 45, the other end 58 of which is freely pivoted about a pin 60 to the lower end 62 of a hydraulic or air cylinder 64. Slidable within the cylinder 64 is a piston 66 which is adapted to reciprocate vertically under the urging of the cylinder. At its upper end, the cylinder 64 is attached through a bracket 68 to the frame.

Upon actuation of the cylinder 64 to move the piston 66 downwardly, the lever arm 45 rotates in the clockwise direction about the pin 48, which raises the vertical shank member 40, and thus the lower rocker link 28 and the ultrasonic testing shoe 30. In its position of maximum extension (not shown) the piston 66 extends downwardly to a point corresponding with the broken-line position 30' of the ultrasonic testing shoe. It will be noted that the ultrasonic testing shoe in the broken-line position in FIG. 1 has its upper surface 70 located above the hot metal plate 14 (i.e. above the hypothetical horizontal plane which is simultaneously tangent to both transporter rolls 12). Naturally, under normal circumstances with the hot metal plate 14 extending fully across the two transporter rolls 12, the ultrasonic testing shoe 30 would not attain its broken-line position in FIG. 1. Instead, it would come into contact or juxtaposition against the under surface of the hot metal plate 14, and the coil spring 54 would have to compress in order to permit the piston 66 to achieve its fully extended condition. The compression of the coil spring 54 would of course exert an upward force against the lower rocker link 28, through the slide bars 27 and against the ultrasonic testing shoe 30, so that there would be a positive force urging the testing shoe 30 against the under surface of the hot metal plate 14.

Figure 3:
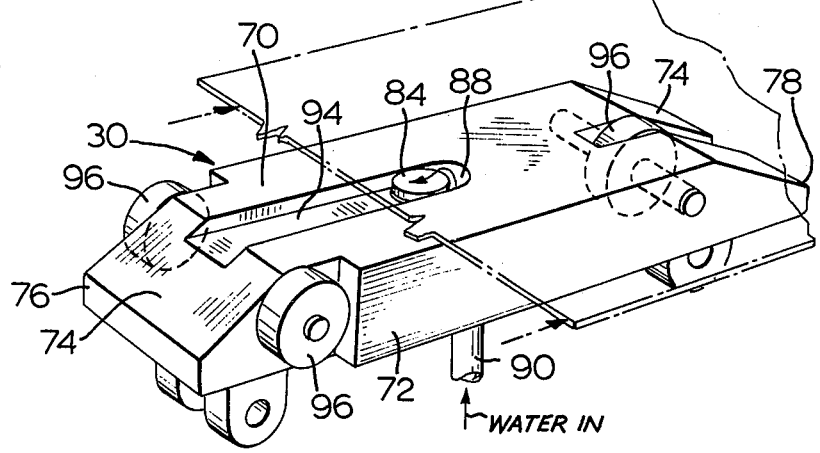
FIG. 3 is a perspective view of an ultrasonic testing shoe of which portions have been broken away to illustrate inner construction.

Attention is now directed to both FIGS. 1 and 3 for a more detailed description of the particular construction of the ultrasonic testing shoe 30. As can be seen, the shoe includes a body member 72 of which the upper surface 70 is adapted to be urged against and into juxtaposition with the under surface of the hot metal plate 14. The upper surface 70 is essentially a flat surface, and the body member 72 includes two bevelled surfaces 74 which slope downwardly away from the hot metal plate 14 at the upstream end 76 and at the downstream end 78 of the ultrasonic testing shoe 30.

Extending centrally and vertically through the body member 72 is an ultrasonic probe member 80, including a signal generating portion 82. It will be noted in FIG. 1 that the generating face 84 of the probe member 80 is substantially parallel with but slightly recessed from the upper surface 70 of the body member 72. A close-fit seal about the surface of the essentially cylindrical probe member 80 is effected at the lower surface of the body member 72, and the body member 72 defines an internal cooling chamber 86 which encircles the probe member 80 and which has an outlet 88 immediately adjacent the generating face 84 of the probe member. Utilizing the movement of the hot metal plate 14 for directional reference, the outlet 88 is located downstream of the generating face 84 of the probe member 80. The body member 72 also effects a tight fit about the probe member 80 at the upper wall of the internal cooling chamber 86, except for the outlet 88.

An inlet pipe 90 communicates with an inlet passageway 92 within the body member 72, both of the latter having the purpose of conveying a cooling liquid to the cooling chamber 86. As shown in FIG. 1, the inlet passageway 92 enters the internal cooling chamber 86 tangentially, the internal cooling chamber 86 in the embodiment shown being essentially cylindrical in configuration. In FIG. 1, a directional arrow has been placed on the drawing to indicate that the cooling liquid, preferably water, would pass through the inlet pipe 90, through the inlet passageway 92, tangentially into the internal cooling chamber 86, circulate around the exterior surface of the probe member 80, and then exit from the internal cooling chamber 86 through the outlet 88. As seen in FIG. 3, the liquid leaving the cooling chamber 86 through the outlet 88 is constrained to pass over the generating face 84, by virtue of the fact that the upper surface 70 is continuous on three sides of the probe member 80, although it is spaced therefrom at the downstream location to allow for the outlet 88.

Upstream of the generating face 84 of the probe member 80 (i.e. to the left in both FIGS. 1 and 3) there is provided a pre-cooling channel 94 which extends through and interrupts the leftward bevelled surface 74. Thus, liquid from the outlet 88 which passes over the generating face 84 can exit through the pre-cooling channel 94, which latter defines a closed conduit with the hot metal plate 14 by virtue of the fact that the upper surface 70 of the body member 72 is juxtaposed against the under surface of the hot metal plate 14.

Attention is now directed to FIGS. 3, 4a, 4b and 4c, for a discussion of the manner in which the particular construction of the ultrasonic testing shoe 30 permits (a) a very close tolerance "fit" between the upper surface 70 of the body member 72 and the under surface of the hot metal plate 14, and (b) an avoidance of the risk that the upper surface 70 of the body member 72 will be worn down on an angle, thus causing the generating face 84 to depart from its parallel relation with the under surface of the hot metal plate 14.

As best seen in FIG. 3, the body member 72 is provided with wheel means which are for the purpose of rolling against the under surface of the hot metal plate 14. More specifically, the wheel means comprises three cylindrical wheels 96, two of the wheels 96 being mounted on the upstream end of the body member 72 with respect to the direction of movement of the hot metal plate 14, and one wheel 96 being mounted on the downstream end, centrally of the body member 72. When the body member 72 is first constructed and assembled, the wheels 96 are not, as might be expected, mounted in such a way that the peripheries extend beyond (above in FIG. 3) the plane defined by the upper surface 70. Instead, as particularly well seen in FIG. 4a, the wheels 96 are initially affixed to the body member 72 such that the peripheries are slightly recessed (downwardly in the figures) with respect to the surface 70, whereby when the ultrasonic testing shoe 30 is first urged against the hot moving metal plate 14, a sliding frictional contact will take place between the upper surface 70 and the under surface of the metal plate 14. Thus, the wheels 96 will not initially rotate, because they will not come into contact with the hot metal plate 14, except possibly for an occassional bit of scale, etc. which may briefly touch one or other of the wheels. Thus, as testing proceeds, with the body member 72 urged upwardly against the under surface of the moving metal plate 14, the upper surface 70 will gradually be worn down, bringing the wheels 96 closed and closer to the metal plate 14. Eventually, the wheels 96 will contact and roll against the metal plate 14, thus arresting the wearing down of the upper surface 70. The initial point of such contact is illustrated in FIG. 4b, from which it will be seen that the wheels 96 are now tangent to the under surface of the hot metal plate 14.

Figure 4A:
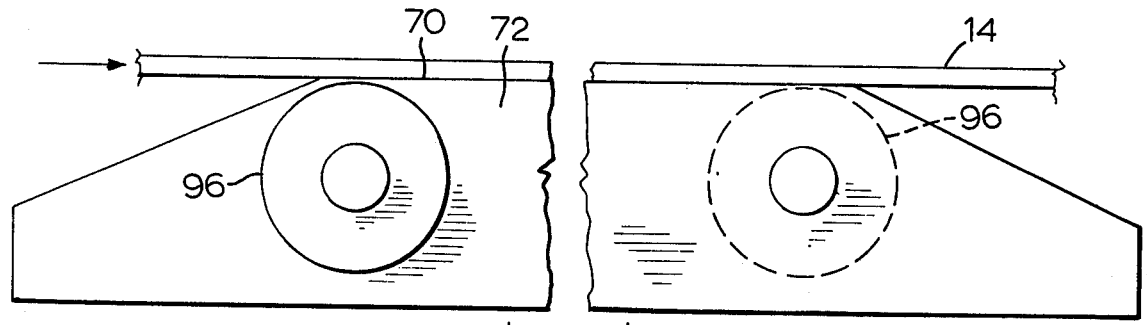
FIGS. 4a, 4b and 4c are sequential views of an ultrasonic testing shoe illustrating sequential steps in the method of ensuring a close tolerance between the moving metal plate and the stationary shoe.
Figure 4B:
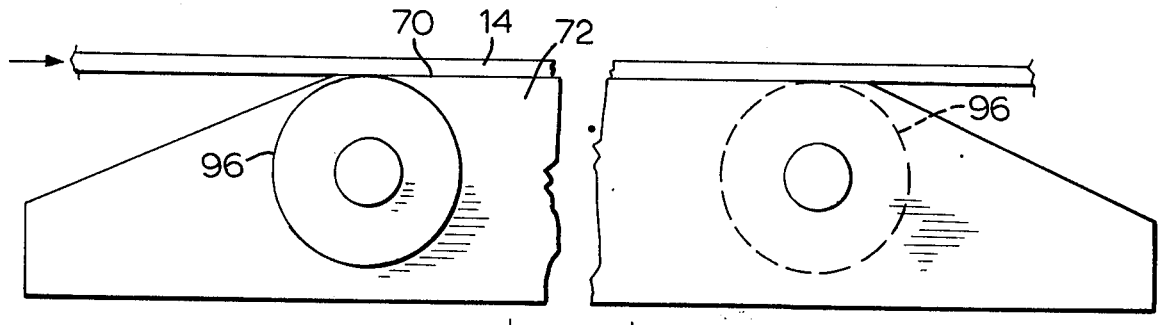
Figure 4C:
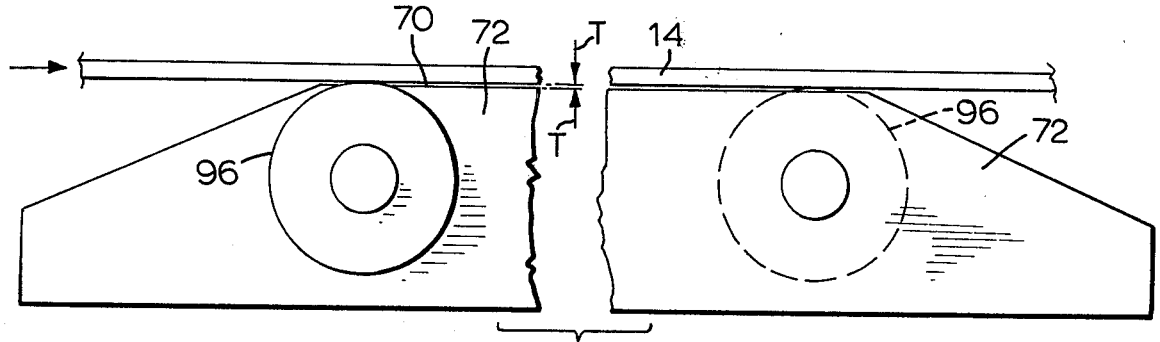

As testing continues beyond the point shown in FIG. 4b, there will be a certain limited amount of further wear of the upper surface 70 on a sporadic basis, due to scale on the underside of the hot metal plate 14, or to certain irregularities in the hot metal plate 14 which cause its under surface to depart from a true plane. This additional, occasional wearing of the upper surface 70 of the body member 72, however, will only account for one or two thousandths of an inch additional wear, and will not destroy the very close juxtaposition of the surface 70 with the hot metal plate 14. In FIG. 4c the very slight tolerance that will ultimately exist between the body member 72 and the hot metal plate 14 has been exaggerated as shown by the arrows T.

It is to be understood that the wheels 96, when initially mounted on the body member 72, are affixed in such a way that the hypothetical plane which is tangent to the upper peripheries of the wheels is in true parallel relation with the generating face 84 of the probe member 80, and such that there exists the slight recess of the wheels 96 with respect to the initial upper surface 70 of the body member 72. Furthermore, the hypothetical plane which is tangent to the upper peripheries of the wheels 96 when initially mounted is spaced from the generating face 84 of the probe member 80 by the appropriate and desired distance for the proper operation of the ultrasonic probe.

The advantages to be gained from mounting the wheels 96 in this fashion initially are appreciable. Firstly, the particular spacing of the generating face 84 from the ultimate position of the hot metal plate 14 can be established very closely. Secondly, the provision of the wheels themselves avoids any risk that the surface 70 will wear in an uneven manner, resulting in the generating face 84 departing from a true parallel relation with the hot metal plate 14. Thirdly, a very close tolerance between the ultimate position of the upper surface 70 and the hot metal plate 14 is ensured. It will be understood that the latter feature is very useful in that in constrains the cooling water coming out of the outlet 88 to exit along the conduit defined by the pre-cooling channel 94 and the hot metal plate 14. If the tolerance were too great (too loose), much of this water would exit laterally, and any such lost water would not be able to serve any pre-cooling purpose. Lastly, by forcing the upper surface 70 to be worn down to the correct tolerance, one avoids the extremely delicate operation of mounting the wheels 96 initially so that the proper tolerance is achieved. Such mounting would have to be within a few thousandths of an inch, and such exactitude is impractical.

It will be understood that the provision of three wheels 96 gives a triangular purchase against the bottom of the hot metal plate 14, and avoids the risk of unevenness that would be present with four or more rollers.

It has been found that an ultrasonic testing shoe constructed in accordance with this invention is capable of testing plates where the plate temperature lies in the range from about 4°C to about 500°C, while maintaining the temperature of the ultrasonic probe itself between about 4°C and about 38°C. Because the pre-cooling of the plate takes place along the conduit defined between the pre-cooling channel 94 and the plate 14 itself, no additional pre-cooling of the plates is found to be necessary. For this reason, the amount of water consumption necessitated by the testing of the plate is considerably reduced, as is the amount of equipment required for the collecting or wiping of pre-cooling water. Furthermore, the amount of steam generated is considerably reduced, and thus the extent of steam collection equipment is also diminished. Furthermore, personal hazard due to steam and hot water is reduced, and distortion of the plates due to thermal stress gradients is minimized.

What I claim is:

1. A shoe for ultrasonically testing hot, moving metal plate for faults, the shoe comprising:
   a body member having a surface adapted to be juxtaposed with respect to the metal plate,
   an ultrasonic probe member fixed in the body member and having a generating face parallel with and slightly recessed from said surface,
   the body member defining an internal cooling chamber encircling said probe member and having an outlet adjacent one portion of the periphery of the generating face of the probe member, the said portion being less than the full periphery,
   an inlet passageway in said body member for conveying cooling liquid to said cooling chamber,
   and a liquid exit and pre-cooling channel in said surface commencing at and communicating with said outlet of the cooling chamber, passing across said generating face, and extending away from the probe member in a direction remote from said outlet, whereby cooling liquid admitted to said cooling chamber through said inlet passageway can cool said probe member and then pass out of said outlet, across said generating face to permit transmission of the ultrasonic signal to the metal plate, and along the channel to cool the metal plate.

2. The invention claimed in claim 1, in which the body member is beveled at opposite ends.

3. The invention claimed in claim 1, in which the inlet passageway admits cooling liquid tangentially into the cooling chamber to induce a swirl therein.

4. The invention claimed in claim 1, in which wheel means are mounted on said body member, said wheel means having peripheries for contacting and rolling on said metal plate but being initially affixed to the body member such that the contacting portions of the peripheries are slightly recessed with respect to said surface of the body member, whereby when the shoe is urged against the moving metal plate said surface is gradually worn down until said peipheries of the wheel means contact the metal plate and restrain further wearing down of said surface.

5. Apparatus for ultrasonically testing hot metal plate for faults, comprising:
   meams for supporting the metal plate for movement in a direction parallel with the plane of the metal plate,
   a shoe which includes a body member having a surface adapted to be juxtaposed against the moving metal plate,
   means for resiliently urging the shoe against the moving metal plate,
   an ultrasonic probe member fixed in the body member and having a generating face parallel with and slightly recessed from said surface,
   an internal cooling chamber within said body member and encircling said probe member,
   an outlet from said chamber adjacent one portion of the periphery of the generating face of the probe member and located downstream of the probe member with respect to the direction of movement of the metal plate, said portion being less than the full periphery,
   an inlet passageway in said body member for conveying cooling liquid to said cooling chamber,
   and a liquid exit and pre-cooling channel in said surface commencing at and communicating with said outlet of the cooling chamber, passing across said generating face, and extending away from the probe member in the upstream direction with respect to the movement of the metal plate, whereby cooling liquid admitted to said cooling chamber through said inlet passageway can cool said probe member and then pass out of said outlet, across said generating face to permit transmission of the ultrasonic signal to the metal plate, and along said channel to pre-cool the metal plate immediately upstream of its passage adjacent the generating face of the probe member.

6. The invention claimed in claim 5, in which the body member is beveled away from the metal plate at both the upstream and downstream edges of the body member.

7. The invention claimed in claim 5, in which the metal plate moves in a horizontal plane, and in which the shoe is urged against the underside of the metal plate.

8. The invention claimed in claim 7, in which the inlet passageway is disposed substantially tangentially with respect to the cooling chamber.

9. The invention claimed in claim 8, in which three wheels are mounted on said body member, said wheels having peripheries for contacting and rolling on said metal plate but being initially affixed to the body member such that the peripheries are slightly recessed with respect to said surface of the body member, whereby when the shoe is urged against the moving metal plate said surface is gradually worn down until said peripheries of the wheels contact and roll against the metal plate and arrest the wearing down of said surface.

10. In a method of ultrasonically testing a hot, moving metal plate for faults, the steps of:
   resiliently urging against one surface of the moving metal plate a flat surface of a body member in which is mounted an ultrasonic probe member having a generating face slightly recessed from the flat surface and thus spaced from said moving metal plate,
   passing cooling liquid continuously into a cooling chamber within said body member and encircling said probe member, thereby cooling said probe member,
   passing cooling liquid out of said chamber through an outlet in said flat surface adjacent and downstream of said probe member with respect to the direction of movement of the metal plate,
   passing cooling liquid from said outlet across said generating face to permit transmission of ultrasonic signals to the moving metal plate,
   and passing the cooling liquid from said generating face along a channel recessed in said flat surface, the channel communicating with said outlet across the generating face and extending upstream with respect to the direction of movement of the metal plate, the cooling liquid thus pre-cooling the hot metal plate before it comes adjacent said generating face.

11. The invention claimed in claim 10, in which the cooling liquid is admitted tangentially into the cooling chamber to promote swirling of the liquid therein.

12. A shoe for testing moving metal plate, the shoe comprising:

a body member having a surface adapted to be juxtaposed with respect to the moving metal plate, wheel means mounted on said body member, said wheel means having peripheries for contacting and rolling on said metal plate but being affixed to the body member such that the contacting portions of the peripheries are slightly recessed with respect to said surface of the body member, whereby when the shoe is urged against the moving metal plate said surface is gradually worn down until said peripheries of the wheel means contact the metal plate and restrain further wearing down of said surface, thereby to ensure that a close fit will ultimately occur between said surface and said moving metal plate while said wheel means are rolling against said moving metal plate.

13. The invention claimed in claim 12, in which the wheel means comprises three wheels mounted on said body member in triangular relationship.

14. The invention claimed in claim 12, in which the body member is beveled away from the metal plate at both the upstream and downstream edges of the body member with respect to the direction of plate movement.

15. A method of ensuring a close tolerance between a moving metal plate and a substantially stationary shoe intended for testing the moving metal plate and having a surface adapted to be juxtaposed with respect to the metal plate, the method comprising the steps:

mounting freely-rotating rolling members on the shoe such that the peripheries of the rolling members are slightly recessed with respect to said surface of the shoe, and urging the shoe resiliently against the moving metal plate to gradually wear down said surface until the peripheries of the rolling members contact and roll against the metal plate, and thus restrain further wearing down of said surface.

16. The method claimed in claim 15, which includes the mounting of three rolling members on the shoe.

* * * * *